United States Patent [19]

Shibata et al.

[11] Patent Number: 4,952,903

[45] Date of Patent: Aug. 28, 1990

[54] CERAMIC HEATER HAVING PORTIONS CONNECTING HEAT-GENERATING PORTION AND LEAD PORTIONS

[75] Inventors: Kazuyoshi Shibata, Nagoya; Hitoshi Nishizawa, Iwakura, both of Japan

[73] Assignee: NGK Insulators, Ltd., Nagoya, Japan

[21] Appl. No.: 299,531

[22] Filed: Jan. 23, 1989

[30] Foreign Application Priority Data

Jan. 28, 1988 [JP] Japan .................................. 63-17729

[51] Int. Cl.⁵ .............................................. H01L 7/00
[52] U.S. Cl. .......................................... 338/34; 73/23; 73/31.05; 204/426; 219/553
[58] Field of Search .............. 338/34, 35; 73/23, 23.1; 204/426, 427; 219/555, 522, 543

[56] References Cited

U.S. PATENT DOCUMENTS

| | | | |
|---|---|---|---|
| 4,138,881 | 2/1979 | Isenberg | 338/34 X |
| 4,579,643 | 4/1986 | Mase et al. | 204/426 |
| 4,588,494 | 5/1986 | Kato et al. | 204/426 |
| 4,655,901 | 4/1987 | Mase et al. | 204/427 |

*Primary Examiner*—Bruce A. Reynolds
*Assistant Examiner*—Marvin Lateef
*Attorney, Agent, or Firm*—Arnold, White & Durkee

[57] ABSTRACT

A ceramic heater including a ceramic body and a heater element formed on the ceramic body. The heater element has a heat-generating portion formed of a cermet containing a ceramic material and a metal material which principally consists of at least one noble metal, electrical lead portions formed of a metallic material which principally consists of at least one base metal, or formed of a cermet containing a ceramic material and said metallic material, and connecting portions connecting said heat-generating portion to said electrical lead portions.

14 Claims, 4 Drawing Sheets

4,952,903

CERAMIC HEATER HAVING PORTIONS CONNECTING HEAT-GENERATING PORTION AND LEAD PORTIONS

BACKGROUND OF THE INVENTION

1. Field of the Invention

The present invention relates to a ceramic heater, an electrochemical element using the ceramic heater, and an oxygen analyzing device having such an electrochemical element. More particularly, the present invention is concerned with such a ceramic heater which is economical to manufacture and highly durable in operation.

2. Discussion of the Prior Art

There is known a ceramic heater which has a heater element including a heat-generating portion and electrical lead portions for supplying power to the heat-generating portion. These heat-generating portion and the electrical lead portions are formed integrally with a ceramic body or substrate. The heater element, i.e., a mass of the heat-generating and lead portions, is formed of a single electrically conductive metal. For example, an inexpensive ceramic heater uses a comparatively inexpensive non-noble or base metal such as tungsten and molybdenum, for the heater element. However, such a ceramic heater suffers from a problem. More specifically, the base metal of the heat-generating portion of the heater element tends to be oxidized during a long period of use of the heater at a high operating temperature in an oxidizing atmosphere such as air. The oxidation may result in disconnection of the heat-generating portion.

In the light of the above drawback, it has been proposed to form the heater element of a noble metal such as platinum and rhodium. While the use of such a noble metal successfully overcomes the electrical disconnection of the heater element, it necessarily increases the cost of manufacture of the ceramic heater, since the noble metal is considerably more expensive that the base metal. This problem of increase in the material cost is serious in view of the recent tendency for the electrical lead portions to have a comparatively large cross sectional area, for lowering the electrical resistance of the lead portions for efficient consumption of electric power by the heat-generating portion to generate heat. Namely, the lead portions require the use of an accordingly large amount of noble metal, which means an increased material cost of the ceramic heater. Further, it is generally difficult to bond a noble metal to a ceramic substrate with a sufficient adhesive or bonding force, and the terminal parts of the electrical lead portions connected to external lead wires or conductors tend to be easily separated from the ceramic substrate.

SUMMARY OF THE INVENTION

It is therefore a first object of the present invention to provide a ceramic heater having a heater element integrally formed on a ceramic body, which heater is economical to manufacture with the amount of use of a noble metal or metals being significantly reduced, and has improved durability at a high operating temperature, being free of the conventionally experienced disconnection of the heater element.

It is a second object of the invention to provide such a ceramic heater wherein the bonding strength of the heater element with respect to the external lead wires is significantly improved.

A third object of the invention is to provide an electrochemical element using the above-indicated ceramic heater, or an oxygen analyzing device using such an electrochemical element, which electrochemical element or oxygen analyzing device is reliable in operation and economical to manufacture.

The first and second objects indicated above may be achieved according to one aspect of the present invention, which provides a ceramic heater comprising a ceramic body and a heater element formed on the ceramic body. The heat element includes a heat-generating portion formed of a cermet containing a ceramic material and a metal material which principally consists of at least one noble metal; electrical lead portions formed of a metallic material which principally consists of at least one base metal, or formed of a cermet containing a ceramic material and the metallic material; and connecting portions connecting the heat-generating portion to the electrical lead portions.

In the ceramic heater of the present invention constructed as described above, the heat-generating portion of the heater element is formed by firing a cermet containing a suitable ceramic material, and a metal material which principally consists of a noble metal or metals. Accordingly, the heat-generating portion is effectively protected from the conventional encountered electrical disconnection at an elevated operating temperature. That is, the durability of the heat-generating portion is improved. Further, the cost of manufacture of the instant ceramic heater is significantly reduced, since the electrical lead portions are formed of a metallic material which principally consists of inexpensive base metal or metals, or a cermet containing a suitable ceramic material and the above-indicated metallic material including the base metal or metals.

Each of the connecting portions of the heater element may consist of an end portion of the heat-generating portion, and an end portion of a corresponding one of the electrical lead portions. The end portions of the heat-generating portion and the corresponding electrical lead portion are superposed on each other in mutually contacting relation. Alternatively, each connecting portion may substantially consist of an alloy of the noble metal of the heat-generating portion and the base metal of the electrical lead portions. Further alternatively, each connecting portion may consist of a cermet which comprises an alloy whose major components consist of the noble metal of the heat-generating portion and the base metal of the electrical lead portions. According to still a further alternative form of the invention, each connecting portion of the heater element may consist of at least one connecting member which connects the heat-generating member and a corresponding one of the electrical lead portions. In this case, each connecting member may be formed of a material which includes a noble metal, a base metal or an alloy of the noble and base metals.

Preferably, at least a portion of a surface of the ceramic body on which the heater element is formed is covered by an electrically insulating ceramic layer. More preferably, at least the heat-generating portion of the heater element is embedded in an electrically insulating ceramic mass.

At least the heat-generating portion of the heater element may be formed integrally with the ceramic body, by co-firing of the heat-generating portion with the ceramic body. In this instance, the high-temperature durability of the heat-generating portion is further improved.

Preferably, platinum is used as the noble metal or one of the noble metals for the heat-generating portion of the heater element. Further, the electrical lead portions may preferably be formed of a cermet containing a ceramic material and a metallic material which principally consists of at least one base metal. Nickel is preferably used as the base metal or one of the base metals for the lead portions. In this case, the lead portions may be fired in the air.

The ceramic heater according to one aspect of the invention described above may be suitably used for various purposes, for example, as a glow plug, a burner ignitor, and heaters for various gas sensors. In particular, the instant ceramic heater is advantageously used as a heater for heating an electrochemical element of gas sensors such as an oxygen sensor adapted to determine or measure the oxygen concentration in exhaust gases of internal combustion engines for automotive vehicles. Such an electrochemical element has at least one electrochemical cell each of which includes a solid electrolyte body, and at least one pair of electrodes formed on the solid electrolyte body. The instant ceramic heater is positioned in the electrochemical element so that the electrochemical cell or cells is/are effectively heated by the ceramic heater.

That is, the third object indicated above may be attained according to another aspect of the invention, which provides an electrochemical element, comprising: at least one electrochemical cell each having a solid electrolyte body and at least one pair of electrodes formed on the solid electrolyte body; and a ceramic heater comprising a ceramic body, and a heater element formed on the ceramic body. The heater element includes (a) a heat-generating portion formed of a cermet containing a ceramic material and a metal material which principally consists of at least one noble metal, (b) electrical lead portions formed of a metallic material which principally consists of at least one base metal, or formed of a cermet containing a ceramic material and the metallic material, and (c) connecting portions connecting the heat-generating portion to the electrical lead portions.

The electrochemical element may be suitably used for an oxygen detecting or analyzing device. That is, the ceramic heater of the invention may be used for such an oxygen analyzing device.

In other words, the third object indicated above may be accomplished according to a further aspect of the present invention, which provides an oxygen analyzing device, comprising: an electrochemical element which comprises at least one electrochemical cell and a ceramic heater, each electrochemical cell having a solid electrolyte body and at least one pair of electrodes formed on the solid electrolyte body; and a ceramic heater comprising a ceramic body, and a heater element formed on the ceramic body, the heater element including (a) a heat-generating portion formed of a cermet containing a ceramic material and a metal material which principally consists of at least one noble metal, (b) electrical lead portions formed of a metallic material which principally consists of at least one base metal, or formed of a cermet containing a ceramic material and the metallic material, and (c) connecting portions connecting the heat-generating portion to the electrical lead portions.

BRIEF DESCRIPTION OF THE DRAWINGS

The above objects, features and advantages of the present invention will be better understood by reading the following detailed description of presently preferred embodiments of the invention, when considered in connection with the accompanying drawings, in which.

DETAILED DESCRIPTION OF THE PREFERRED EMBODIMENTS

Figure 1:
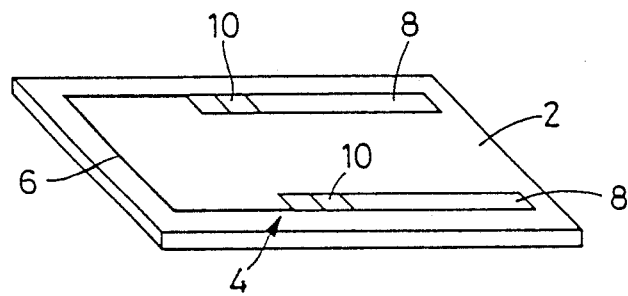
FIG. 1 is a schematic perspective view showing a simplest form of a ceramic heater of the present invention.

Referring first to FIG. 1, reference numeral 2 denotes a ceramic body in the form of a ceramic substrate. On one of opposite surfaces of this ceramic substrate 2, there is integrally formed a heater element indicated generally at 4. The heater element 4 includes a heat-generating portion 6 adapted to generate heat upon energization thereof, and two electrical lead portions 8, 8 for connecting the heat-generating portion 6 to an external electric power source (not shown), to supply power to the heat-generating portion 6. The heater element 4 further includes two connecting portions 10, 10 which electrically connect the opposite ends of the heat-generating portion 6 to the respective electrical lead portions 8, 8.

The heat-generating portion 6 of the heater element 4 is formed of a cermet containing a suitable ceramic material, and a metal material which principally consists of at least one noble metal. Namely, an unfired layer of the heat-generating portion 6 is co-fired with an unfired body of the ceramic substrate 2, so that the heat-generating portion 6 is formed as an integral part of the substrate 2, whereby the durability of the portion 6 at an elevated operating temperature of the heater is improved. The co-firing operation is usually performed in the air. The noble metals which may be used for the heat-generating portion 6 are selected from the group of platinum metals such as platinum, rhodium, palladium, ruthenium, osmium and iridium. The ceramic materials used for the cermet are preferably selected from those materials which are similar to that of the ceramic substrate 2, from the standpoint of bonding strength between the heat-generating element 6 and the ceramic substrate 2.

The electrical lead portions 8, 8 of the heater element 4 are formed of a metallic material which principally consists of at least one base or non-noble metal, or formed of a cermet which contains a suitable ceramic material and the metallic material containing a base metal or metals. The base metals which may be used for the lead portions 8 are selected from the group which includes aluminum, titanium, chromium, manganese, iron, cobalt, nickel and copper, as well as metals having a high melting point such as niobium, molybdenum, tantalum and tungsten.

The connecting portions 10, 10 connecting the heat-generating portion 6 and the electrical lead portions 8 may take various forms, as illustrated in FIGS. 2(a) through 2(e). In these figures, only one of the two connecting portions 10, 10 which is connected to one end of the heat-generating portion 6 is shown.

Figure 2A:
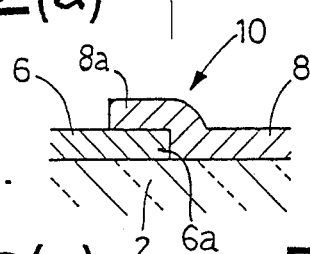
FIGS. 2(a) through 2(e) are fragmentary elevational views in cross section of different forms of connecting portions which connect a heat-generating portion and electrical lead portions of a heater element of the ceramic heater.
Figure 2B:
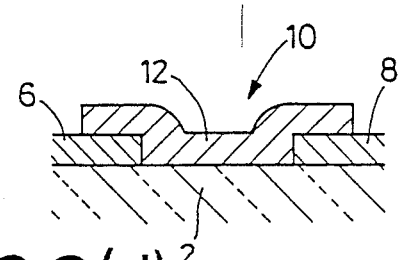
Figure 2C:
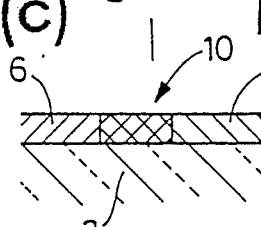
Figure 2D:
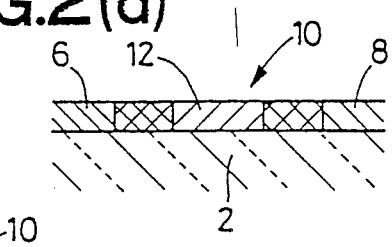

The connecting portion 10 shown in FIG. 2(a) consists of an end portion 6a of the heat-generating portion 6, and a corresponding end portion 8a of the lead portion 8. The end portions 6a, 8a are superposed on each other in mutually contacting relation. The connecting portion 10 shown in FIG. 2(b) consists of one connecting member 12 which engages the corresponding end portions of the heat-generating and lead portions 6, 8. The connecting member 12 is formed of a noble metal or a base metal, or an alloy of noble and base metals. The connecting member 12 may be formed of a cermet which includes a suitable ceramic material, and such noble or base metal or an alloy thereof.

Where a noble metal layer and a base metal layer are superposed on each other and fired at a high temperature, these metals are alloyed. Examples of such alloyed connecting portions 10 are illustrated in FIGS. 2(c) and 2(d). In the figures, cross hatching zones indicate the alloyed portions. The alloyed portions 10 of FIG. 2(c) and 2(d) are prepared by firing the connecting portions 10, 10 of FIGS. 2(a) and 2(b), respectively. It will be understood that alloyed portions as indicated by the cross hatching in FIGS. 2(c) and 2(d) may be formed of a suitable alloy or a material containing the alloy, without alloying the mutually superposed portions as indicated in FIGS. 2(a) and 2(b).

Figure 2E:
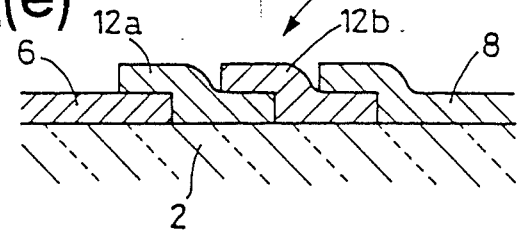

Alternatively, the connecting portion 10 may consist of a plurality of connecting members, e.g., two connecting members 12a, 12b as indicated in FIG. 2(e), which are disposed between the corresponding ends of the heat-generating and lead portions 6, 8. The composition of the array of the connecting members 12a, 12b, . . . varies gradually from the end adjacent to the heat-generating portion 6 toward the other end adjacent to the lead portion 8. More specifically, the content of the noble metal decreases in the direction from the heat-generating portion 6 toward the lead portion 8, while the content of the base metal decreases in the direction from the lead portion 8 toward the heat-generating portion 6.

The selected materials for the heat-generating portion 6, lead portions 8 and connecting portions 10 of the heater element 4 are applied to the ceramic substrate 2 in a predetermined pattern, by a suitable known technique such as a screen printing method. The applied unfired pattern of the materials is suitably fired or baked, so that the heater element 4 is formed integrally with the ceramic substrate 2. For improved durability of the ceramic heater, it is desirable that the lead portions 8 as well as the heat-generating portion 6 are co-fired with the ceramic substrate 2. In this case, the firing in the air is difficult, and is therefore usually effected in a neutral or reducing atmosphere. Where the heat-generating and lead portions 6, 8 are co-fired with the ceramic substrate 2, the connecting portions 10 connecting these portions 6, 8 are likely to be an alloy of the noble and base metals during exposure to a high sintering temperature. In this respect, it is necessary to take account of the stability of the alloy, in determining the firing and other conditions.

It is possible, however, that only the heat-generating portion 6 is co-fired with the ceramic substrate 2, and the lead portions 8 are subsequently applied to and fired on the fired ceramic substrate. In this case, the connecting portions 10 are less likely to be an alloy of the noble and base metals, since the firing temperature of the lead portions 8 is usually lower than the sintering temperature of the ceramic material of the ceramic substrate 2. Thus, the electrical connection between the heat-generating and lead portions 6, 8 by the connecting portions 10 is achieved by mere contacts of the connecting portions 10 to the portions 6, 8, or by means of thin alloyed layers formed adjacent to the interface between the connecting portions 10 and the portions 6, 8. In this instance, the lead portions 8 may be formed solely of a base metal or metals, or formed of a cermet comprising a base metal or metals and a ceramic material. Where only the base metal or metals is/are used, it is recommended to apply a glass coating to the lead portions 8, in order to compensate for a relatively small bonding or adhesive force of the base metals to the ceramic substrate 2. The firing of the lead portions 8 may be accomplished at a relatively low temperature, either in the air, or in a neutral or reducing atmosphere.

The ceramic substrate 2 on which the heater element 4 is formed as described above may be formed of a ceramic composition whose principal component is selected from the group including zirconia, alumina, mullite, cordierite, forsterite, beryllia and silicon nitrode, or a mixture thereof. The ceramic substrate 2 may be a ceramic layer formed of the above ceramic composition applied to a surface of a metal sheet. Further, the ceramic substrate 2 preferably takes a planar or sheet configuration as illustrated in FIG. 1, but may be a columnar or other configuration, depending upon the specific requirements of the ceramic heater to be produced.

In the ceramic heater constructed as described above, a comparatively inexpensive base metal or metals is/are used for the electrical lead portions 8, 8 which constitute a considerably large part of the entire mass of the heater element 4, and the amount of use of a noble metal or metals for the heater element is considerably reduced. As a result, the cost of manufacture of the instant ceramic heater is effectively reduced, as compared with that of a ceramic heater whose heater element is entirely formed of a noble metal or metals. Further, the heat-generating portion 6 exposed to a high temperature is formed of a cermet containing a noble metal or metals, and is thus protected from the conventionally experienced disconnection, whereby the durability of the heat-generating portion 6 is significantly improved. It is also important to note that the base metal or metals used for the electrical lead portions 8 provide an intermediate layer at the interface with the surface of the ceramic material of the ceramic substrate 2, thereby increasing the bonding strength with respect to external lead wires, and enhancing the operating reliability of the ceramic heater. The reliability is further enhanced where the base metal is brazed to the external lead wires.

Figure 3:
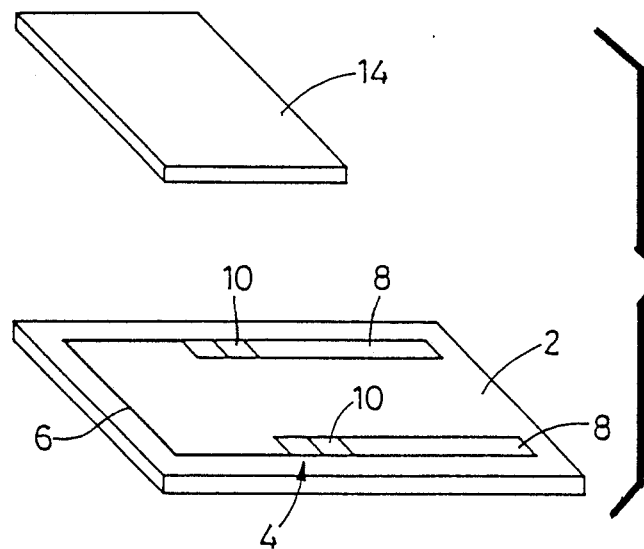
FIGS. 3, 4 and 5, are exploded schematic perspective views of different embodiments of the ceramic heater of the invention.
Figure 4:
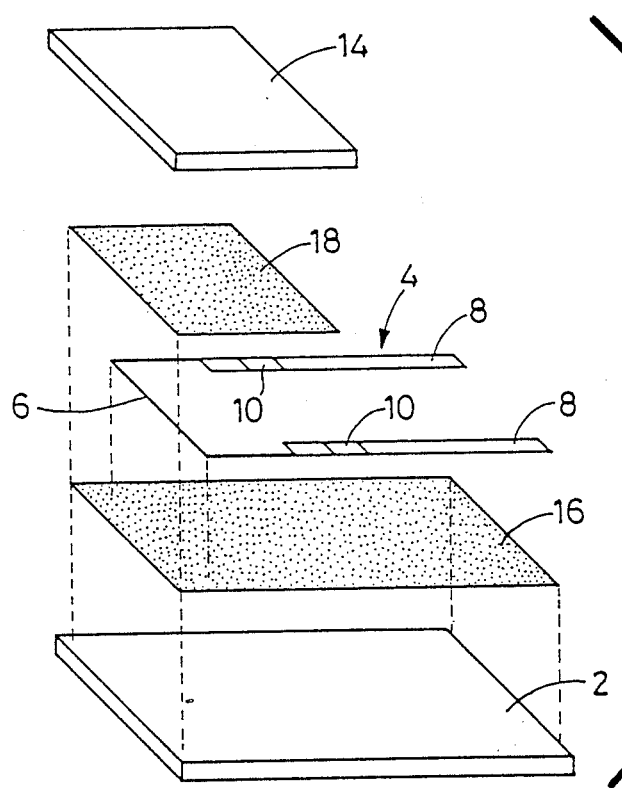
Figure 5:
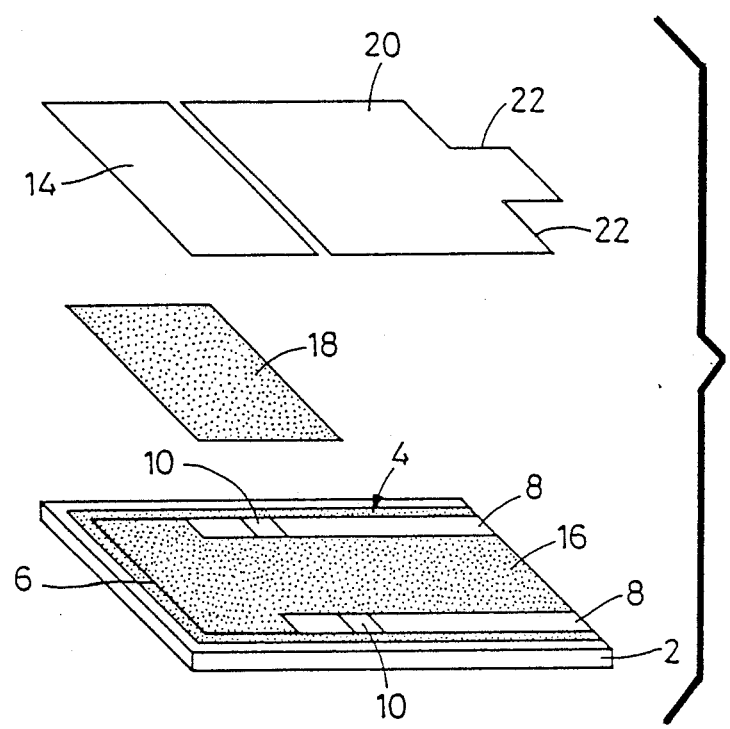

While the simplest form of the ceramic heater according to the present invention has been described, it is to be understood that the invention is not limited to the detailed construction of FIG. 1, but may be embodied with various modifications as illustrated in FIGS. 3-5, and with various changes or improvements which may occur to those skilled in the art.

In the ceramic heater of FIG. 3, the heater element 4 described above is integrally formed on the ceramic substrate 2 formed of alumina, as in the embodiment of FIG. 1. However, the heat-generating portion 6 of the heater element 4 is covered by a protective layer 14 formed of alumina. This protective layer 14 for protecting the heat-generating portion 6 is either a dense layer or alternatively a porous layer. Where the protective layer 14 has a dense structure, the heat-generating portion 6 is suitably protected from volatilization at a high operating temperature, and is effectively protected from an influence by the surrounding atmosphere. Where the protective layer 14 is a porous structure, the layer 14 functions to reduce or minimize deformation of the heat-generating portion 6 due to thermal stresses. In the present specific example wherein the ceramic substrate and protective layer 14 are both made of alumina, the heater element 4 is well electrically insulated.

Reference is now made to FIG. 4 showing another modified embodiment of the invention, wherein the ceramic substrate 2 is formed of zirconia, and the protective layer 14 is a dense ceramic structure also formed of zirconia. Therefore, the electrical insulation of the heater element 4 is necessary, and is achieved by the provision of two porous alumina insulating layers 16, 18 which are disposed such that the heat-generating portion 6 is embedded in the mass of alumina 16, 18, and such that the insulating layer 16 is laminated on the inner surface of the ceramic substrate 2, while the insulating layer 18 is laminated on the inner surface of the dense protective layer 14. According to this arrangement, the heater element 4 is electrically insulated by the porous insulating layer 16 with respect to the ceramic substrate 2, and by the porous insulating layer 18 with respect to the dense protective layer 14.

Referring next to FIG. 5 showing a still further modification of the ceramic heater, the protective layer 14 is a dense zirconia layer which is formed by printing technique, unlike the protective layer 14 of FIG. 4 which is formed by firing a green sheet. Another difference of the present embodiment of FIG. 5 from that of FIG. 4 is the provision of a ceramic protective layer 20 made of a glass or other ceramic material for protecting the electrical lead portions 8, 8 of the heater element 4. The protective layer 20 has two cutouts 22, 22 at the terminal part of the ceramic heater, so that the terminal ends of the lead portions 8 are exposed for electrical connection to the external lead wires leading to the power source.

Figure 6:
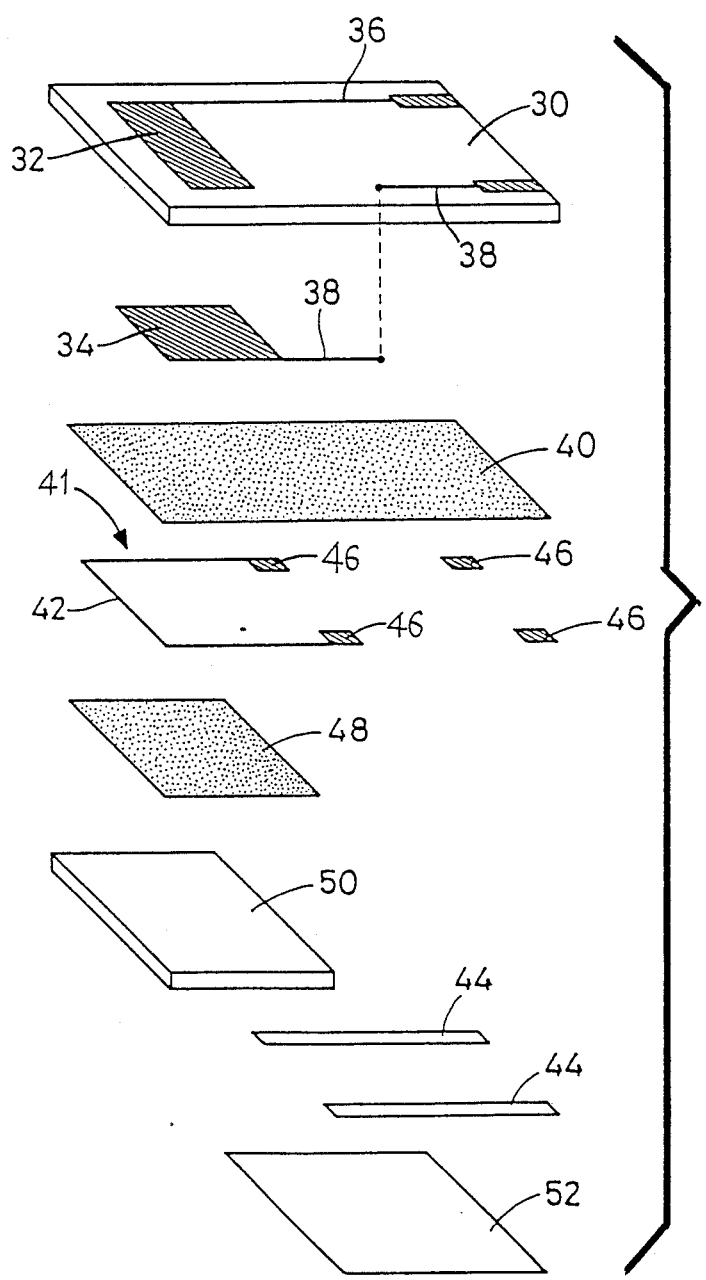
FIG. 6 is an exploded schematic perspective view of one form of an electrochemical element which incorporates a further embodiment of the ceramic heater of the invention.

While the ceramic heater according to the present invention as illustrated above has various industrial applications, one example of the application is shown in FIG. 6, wherein a ceramic heater according to another embodiment of the invention is used for a simplest form of an electrochemical oxygen detecting element or oxygen analyzing device. For efficient heating of the oxygen detecting element or electrochemical cell, the detecting element and the ceramic heater are formed as an integrally sintered body.

Described in greater detail, the electrochemical cell of FIG. 6 which serves as an element for detecting an oxygen concentration in a given measurement gas includes a planar solid electrolyte body 30 made of an oxygen-ion conductive ceramic material such as zirconia, and a pair of electrodes, i.e., a measuring electrode 32 and a reference electrode 34 which are formed on the opposite major surfaces of the solid electrolyte body 30, as well known in the art. The electrodes 32, 34 are connected to an external detecting device through respective lead portions 36, 38. According to the known principle of operation, the oxygen concentration of the atmosphere adjacent to the measuring electrode 32 is measured or determined, as compared with a predetermined reference oxygen concentration on the reference electrode 34, with an electric current flowing from the reference electrode 34 to the measuring electrode 32.

On the inner surface of the electrochemical oxygen concentration cell (30, 32, 34), there is formed a heater element 41 of the invention via a porous alumina structure of an electrically insulating layer 40. The heater element 41 has a heat-generating portion 42, two electrical lead portions 44, 44, and connecting portions 46, 46 for connecting the heat-generating portion 42 to the lead portions 44. The connecting portions 46 are formed of the same material as the heat-generating portion 42. An electrically insulating layer 48 having a porous alumina structure is provided to cover the heat-generating portion 42 of the heater element 41, on the side remote from the insulating layer 40. The insulating layer 48 is formed on the inner surface of a dense zirconia protective layer 50. The electrical lead portions 44 of the heater element 41 are covered by a protective layer 52 made of a glass or similar material.

According to a preferred method of manufacture of the electrochemical element or cell constructed as described above, the solid electrolyte body 30, measuring and reference electrodes 32, 34, lead portions 36, 38, insulating layer 40, heat-generating portion and connecting portions 46 of the heater element 41, insulating layer 48 and protective layer 50 are formed in a suitable lamination or printing method, and are then co-fired. Subsequently, the electrical lead portions 44 are formed so as to be connected to the connecting portions 46, for connection to the heat-generating portion 42. Then, the protective layer 52 is formed to cover the lead portions 44. Thus, the intended electrochemical element incorporating the ceramic heater is produced.

In the instant electrochemical element, the electrochemical cell for detecting oxygen concentration and the ceramic heater are formed as a unitary sintered body, so that the portion of the electrochemical cell including the electrodes 32, 34 is most efficiently heated by the ceramic heater. In the present embodiment, the solid electrolyte body 30 of the electrochemical cell also serves as a ceramic body or substrate on which the heater element 41 is formed. As indicated in FIG. 6, the connecting portions 46 formed of a noble metal or metals are provided at the terminal ends of the lead portions 44 connected to the external lead wires, as well as at the opposite ends of the heat-generating portion 42. Since the noble metal connecting portions 46 are free from surface oxidation, the external lead wires may be connected to the connecting portions 46 at the terminal ends of the lead portions 44, such that the external lead wires are held merely in contact with the appropriate connecting portions 46, as disclosed in Laid-open Publication No. 60-150449 of unexamined Japanese Patent Application.

The heat-generating portion 42 of the heater element 41 is formed of a cermet containing a suitable ceramic material, and a metal material which principally consists of a noble metal such as platinum. Therefore, the heat-generating portion 42 is substantially completely protected from disconnection at an elevated operating temperature. Namely, the heat-generating portion 42 has significantly improved durability. Further, the lead portions 44 are formed of a metallic material which principally consists of a base metal such as nickel, or a cermet which contains such a metallic material and a ceramic material. Since the lead portions 44 are less likely to generate heat and are therefore maintained at a considerably low temperature, the use of the base metal for the lead portions 44 does not cause any problem, and results in significantly reducing the total amount of use of a noble metal or metals for the heater element 41, leading to reduction in the costs of manufacture of the heater element 41 and the electrochemical element using the ceramic heater, and to reduction in the cost of manufacture of the oxygen analyzing device using the electrochemical element.

The material selection according to the invention for the heater element 41 is equally applicable to the lead portions 36, 38 for connecting the electrodes 32, 34 of the electrochemical cell to the external detecting device. Namely, the lead portions 36, 38 may be formed of a metallic material principally consisting of a base metal or metals, or a cermet containing such a metallic material and a ceramic material. In this case, the amount of use of a noble metal or metals for the electrochemical cell may be reduced, whereby the cost of manufacture of the electrochemical element may be further reduced.

While the electrochemical element illustrated in FIG. 6 uses only one electrochemical cell, the principle of the present invention is equally applicable to an electrochemical element which uses a plurality of electrochemical cells adapted to detect or determine the concentration of a given component of a measurement gas. It will be understood that the ceramic heater of the invention may be suitable modified or adapted for various other applications.

It is also to be understood that the invention may be embodied with various other changes, modifications and improvements, which may occur to those skilled in the art, without departing from the spirit and scope of the invention defined in the following claims.

What is claimed is:

1. A ceramic heater comprising:
   a ceramic body; and
   a heater element formed on the ceramic body, said heater element comprising:
   (i) a heat-generating portion formed of a cermet containing a ceramic material and a metal material consisting essentially of at least one noble metal;
   (ii) electrical lead portions formed of a metallic material consisting essentially of at least one base metal, or formed of a cermet containing a ceramic material and said metallic material; and
   (iii) connecting portions connecting said heat-generating portion to said electrical lead portions.

2. A ceramic heater according to claim 1, wherein each of said connecting portions of said heater element consists of an end portion of said heat-generating portion, and an end portion of a corresponding one of said electrical lead portions, said end portions of the heat-generating portion and said corresponding electrical lead portion being superposed on each other.

3. A ceramic heater according to claim 1, wherein each of said connecting portions of said heater element substantially consists of an alloy of said noble metal of said heat-generating portion and said base metal of said electrical lead portions.

4. A ceramic heater according to claim 1, wherein each of said connecting portions of said heater element consists of a cermet which comprises an alloy whose major components consist of said noble metal of said heat-generating portion and said base metal of said electrical lead portions.

5. A ceramic heater according to claim 1, wherein each of said connecting portions of said heater element consists of at least one connecting member connecting said heat-generating portion and a corresponding one of said electrical lead portions.

6. A ceramic heater according to claim 5, wherein said at least one connecting member of said heater element is formed of a material which includes a noble metal, a base metal or an alloy of the noble and base metals.

7. A ceramic heater according to claim 1, wherein at least a portion of a surface of said ceramic body on which said heater element is formed is covered by an electrically insulating ceramic layer.

8. A ceramic heater according to claim 1, wherein at least said heat-generating portion of said heater element is embedded in an electrically insulating ceramic mass.

9. A ceramic heater according to claim 1, wherein at least said heat-generating portion of said heater element is formed integrally with said ceramic body, by co-firing of said heat-generating portion with said ceramic body.

10. A ceramic heater according to claim 1, wherein said at least one noble metal of said heat-generating portion of said heater element includes platinum.

11. A ceramic heater according to claim 1, wherein said electrical lead portions are formed of a cermet containing a ceramic material and a metallic material which consists essentially of at least one base metal, and said at least one base metal includes nickel.

12. A ceramic heater according to claim 1, wherein each of said connecting portions of said heater element consists of at least one connecting member connecting said heat-generating member and a corresponding one of said electrical lead portions, and the amount of noble metal contained in said connecting portions decreases in a direction from said heat-generating portion to said corresponding one of said electrical lead portions.

13. An oxygen analyzing device, comprising:
   an electrochemical element which comprises at least one electrochemical cell, each of said at least one electrochemical cell having a solid electrolyte body and at least one pair of electrodes formed on said solid electrolyte body; and
   a ceramic heater comprising a ceramic body, and a heater element formed on said ceramic body, said heater element including (a) a heat-generating portion formed of a cermet containing a ceramic material and a metal material consisting essentially of at least one noble metal, (b) electrical lead portions formed of a metallic material consisting essentially of at least one base metal, or formed of a cermet containing a ceramic material and said metallic material, and (c) connecting portions connecting said heat-generating portion to said electrical lead portions.

14. An electrochemical element, comprising:
   at least one electrochemical cell each having a solid electrolyte body and at least one pair of electrodes formed on said solid electrolyte body; and
   a ceramic heater comprising a ceramic body, and a heater element formed on said ceramic body, said heater element including (a) a heat-generating portion formed of a cermet containing a ceramic material and a metal material consisting essentially of at least one noble metal, (b) electrical lead portions formed of a metallic material which principally consists of at least one base metal, or formed of a cermet containing a ceramic material and said metallic material, and (c) connecting portions connecting said heat-generating portion to said electrical lead portions.

* * * * *